US011559703B2

(12) United States Patent
Shaw et al.

(10) Patent No.: US 11,559,703 B2
(45) Date of Patent: Jan. 24, 2023

(54) TECHNOLOGIES FOR ENERGY-MODULATED RADIATION THERAPY

(71) Applicant: UNM Rainforest Innovations, Albuquerque, NM (US)

(72) Inventors: Richard Shaw, Albuquerque, NM (US); Shuang Luan, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 314 days.

(21) Appl. No.: 16/762,364

(22) PCT Filed: Nov. 9, 2018

(86) PCT No.: PCT/US2018/060169
§ 371 (c)(1),
(2) Date: May 7, 2020

(87) PCT Pub. No.: WO2019/094824
PCT Pub. Date: May 16, 2019

(65) Prior Publication Data
US 2020/0353288 A1    Nov. 12, 2020

Related U.S. Application Data

(60) Provisional application No. 62/682,530, filed on Jun. 8, 2018, provisional application No. 62/584,267, filed on Nov. 10, 2017.

(51) Int. Cl.
*H05H 7/12* (2006.01)
*A61N 5/10* (2006.01)
*H01J 35/10* (2006.01)

(52) U.S. Cl.
CPC ........... *A61N 5/1047* (2013.01); *A61N 5/103* (2013.01); *A61N 5/1045* (2013.01);
(Continued)

(58) Field of Classification Search
CPC .... A61N 5/1047; A61N 5/103; A61N 5/1042; A61N 5/1045; A61N 5/1048;
(Continued)

(56) References Cited

U.S. PATENT DOCUMENTS

| 5,734,168 A * | 3/1998 | Yao ................... A61N 5/10 315/5.41 |
| 9,245,657 B2 * | 1/2016 | Saito ................... G21K 1/00 |
| 2004/0082855 A1 * | 4/2004 | Robar .................. A61N 5/10 600/436 |

(Continued)

FOREIGN PATENT DOCUMENTS

WO    WO-2019094824 A1    5/2019

OTHER PUBLICATIONS

Otto, K. (2007). Volumetric modulated arc therapy: IMRT in a single gantry arc. Medical Physics, 35(1), 310-317. https://doi.org/10.1118/1.2818738 (Year: 2007).*

(Continued)

*Primary Examiner* — Thaddeus B Cox
*Assistant Examiner* — Marc D. Honrath
(74) *Attorney, Agent, or Firm* — Schwegman Lundberg & Woessner, P.A.

(57) ABSTRACT

Described are devices, systems, and methods for modulating the spectral energy distribution produced by an x-ray source via control of the energy of the x-ray-generating electron beam, e.g., for energy-modulated radiation therapy or other purposes. In some embodiments, such energy modulation is achieved by an add-on device to a linear accelerator. Also disclosed are computational methods and computer program products for planning energy-modulated therapy.

17 Claims, 13 Drawing Sheets

(52) U.S. Cl.
CPC ......... *A61N 5/1048* (2013.01); *A61N 5/1081* (2013.01); *H01J 35/106* (2013.01); *H05H 7/12* (2013.01); *A61N 2005/1089* (2013.01); *A61N 2005/1095* (2013.01); *H01J 2235/1204* (2013.01)

(58) Field of Classification Search
CPC .......... A61N 5/1081; A61N 2005/1089; A61N 2005/1095; H01J 35/106; H01J 2235/1204; H05H 7/001; H05H 7/12; H05H 2007/004; H05H 2277/11
See application file for complete search history.

(56) References Cited

U.S. PATENT DOCUMENTS

| | | | |
|---|---|---|---|
| 2007/0018111 A1* | 1/2007 | Calderon | G21K 5/04 250/393 |
| 2010/0051833 A1* | 3/2010 | Guertin | H05H 7/12 250/515.1 |
| 2010/0310045 A1* | 12/2010 | Brown | H01J 35/00 378/65 |
| 2016/0193482 A1* | 7/2016 | Fahrig | H05H 9/048 600/1 |
| 2017/0050046 A1* | 2/2017 | Walder | A61N 5/062 |
| 2018/0277276 A1* | 9/2018 | Purwar | A61N 5/1043 |

OTHER PUBLICATIONS

"International Application Serial No. PCT/US2018/060169, International Search Report dated Mar. 7, 2019", 2 pgs.

"International Application Serial No. PCT/US2018/060169, Written Opinion dated Mar. 7, 2019", 5 pgs.

"International Application Serial No. PCT/US2018/060169, International Preliminary Report on Patentability dated May 22, 2020", 7 pgs.

* cited by examiner

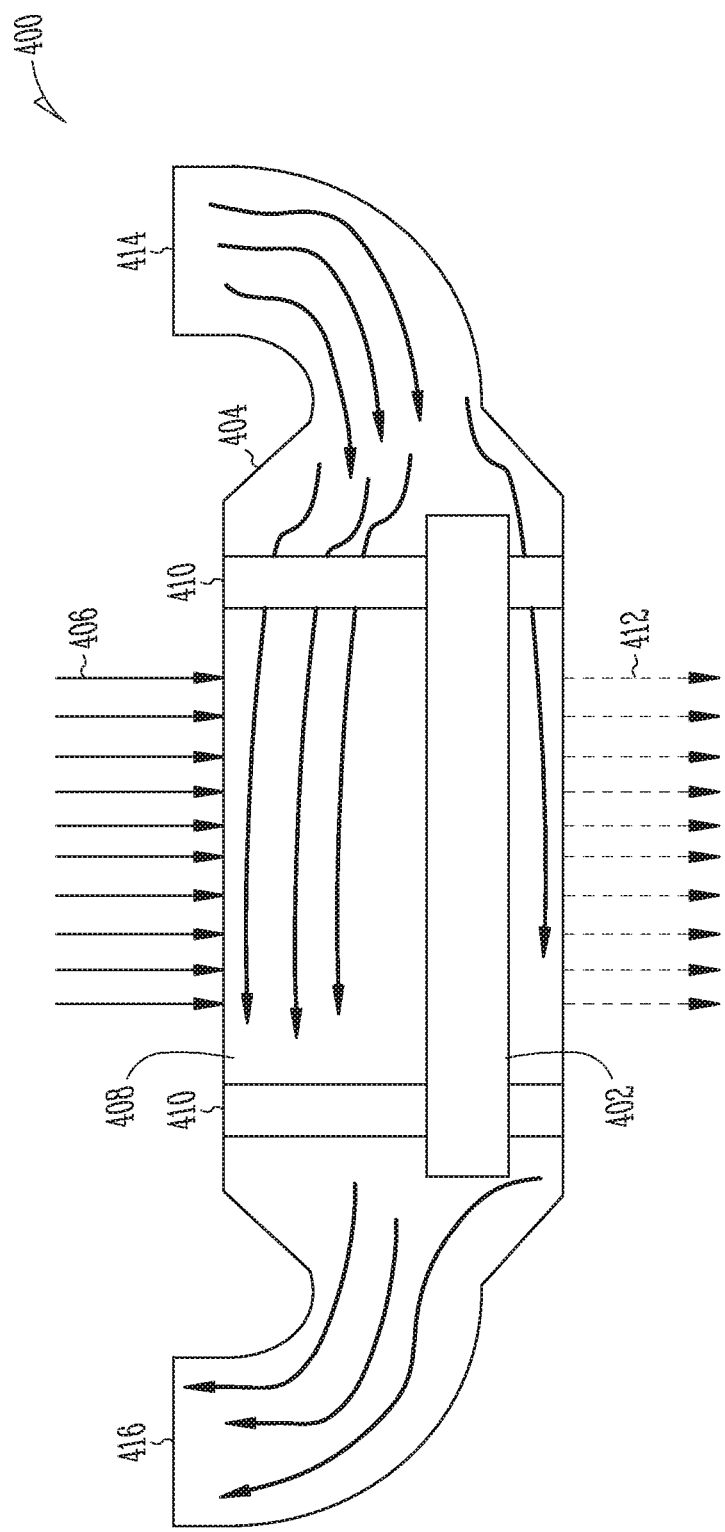

TECHNOLOGIES FOR ENERGY-MODULATED RADIATION THERAPY

CROSS-REFERENCE TO RELATED APPLICATIONS

This application is a U.S. National Stage Filing under 35 U.S.C. 371 from International Application No. PCT/US2018/060169, filed on Nov. 9, 2018, and published as WO 2019/094824 on May 16, 2019, which application claims the benefit of priority to U.S. Provisional Patent Application Ser. No. 62/584,267, filed Nov. 10, 2017 and entitled "Radiation Therapy Technologies," and U.S. Provisional Patent Application No. 62/682,530, filed Jun. 8, 2018 and entitled "Energy-Modulated Arc Therapy Through Energy Blending," which are hereby incorporated herein by reference in their entireties.

TECHNICAL FIELD

This disclosure relates to controlled x-ray generation and its application to radiation therapy.

BACKGROUND

Radiation therapy has long been used to shrink and/or kill cancerous tissue through exposure to high doses of high-energy radiation. A device commonly employed in radiation therapy is a linear accelerator (LINAC), which accelerates charged particles, such as protons, electrons, or ions, to high energies, and uses them either directly as the therapeutic beam, or converts them to other forms of radiation. In x-ray therapy, for instance, a high-energy (e.g., 6 MeV) electron beam generated in the LINAC may be directed onto an x-ray converter target, such as a sheet of tungsten or another heavy metal, to create, via interactions of the electrons with the target, a distribution of x-rays with energies up to the energy of the incident electrons. The LINAC may be mounted within a gantry that can be rotated around a patient to allow irradiating the treatment target, such as a tumor, from different angles to thereby accumulate absorbed radiation doses primarily within the treatment target.

Over the years, radiation therapy, and in particular x-ray therapy, has undergone significant development geared towards improving the conformity of the delivered dose to the treatment target to maximize treatment efficacy while minimizing damage to healthy tissue. One by now established technique serving this purpose is intensity-modulated radiation therapy (IMRT), which allows varying the intensity and shape of the x-ray beam between different angles from which the beam is directed onto the treatment target.

While conventional static-field IMRT provides a selection among a small number (e.g., 5-11) discrete beam angles and stops irradiation in between beam movements, the more recently developed volumetric modulated arc therapy (VMAT) mode enables continuous x-ray delivery along with dynamic intensity and beam-shape manipulations as the beam is swung in a full or partial arc around the patient. Using a multi-leaf collimator (MLC) to create small apertures in conjunction with treatment planning to optimize the beam as a function of angle, state-of-the-art techniques like VMAT have been able to reduce treatment areas from formerly $cm^2$ to $mm^2$, drastically improving the degree to which the dose distribution can be conformed to geometrically complex treatment targets while avoiding surrounding normal tissue. As the push towards smaller and smaller treatment areas continues, however, existing techniques and tools have reached a practical ceiling imposed by the physics of high-energy photons and, in particular, the minimum dose gradients achievable with the photon energies produced by current LINACs.

BRIEF DESCRIPTION OF THE DRAWINGS

Various example embodiments of the disclosed subject matter are herein described with reference to the accompanying drawings, in which:

FIG. 4 is a schematic diagram of an example energy-modulating x-ray converter target module including a converter target layer movable within a water-filled moderator chamber in a direction of an impinging electron beam, in accordance with various embodiments;

DESCRIPTION

Described herein are devices, systems, and methods for modulating, via the energy of x-ray-generating electrons, the spectral energy distribution of an x-ray beam, as well as for exploiting this capability in energy-modulated radiation therapy. In various embodiments, an electron-energy modulator is retrofitted to an existing LINAC to allow the x-ray spectrum to be changed on demand without otherwise altering the function of the LINAC. In this manner, x-ray beams with lower photon-energy distributions than ordinarily produced by LINACs, yet with comparably high photon yields, can be obtained. Beneficially, in radiation therapy, lower x-ray energies allow for steeper dose gradients and, thus, enable smaller treatment areas and better target conformity of the delivered radiation dose. Embodiments described herein further allow blending multiple spectral energy distributions, e.g., by irradiating the treatment target sequentially from the same direction with beams differing in their spectral energy distribution, or by directing beams with different spectral energy distributions from multiple angles onto the treatment target. Blending spectral energies can improve the trade-off between, on the one hand, deeper penetration, which is achieved by higher-energy photons, and, on the one hand, steeper gradients, which are achieved by lower-energy photons. In some embodiments, energy modulation in accordance herewith is performed dynamically during treatment, e.g., as the beam is moved around the treatment target in an arc, and in conjunction with intensity modulation; in such "energy-modulated VMAT," the spectral energy of the x-rays provides an additional adjustable parameter (compared with IMRT) for optimizing the dose distribution in a patient. Computational methods and computer program products for planning energy-modulated treatment of a given treatment target are also disclosed herein.

Various example embodiments will now be described with reference to the accompanying drawings.

Figure 1:
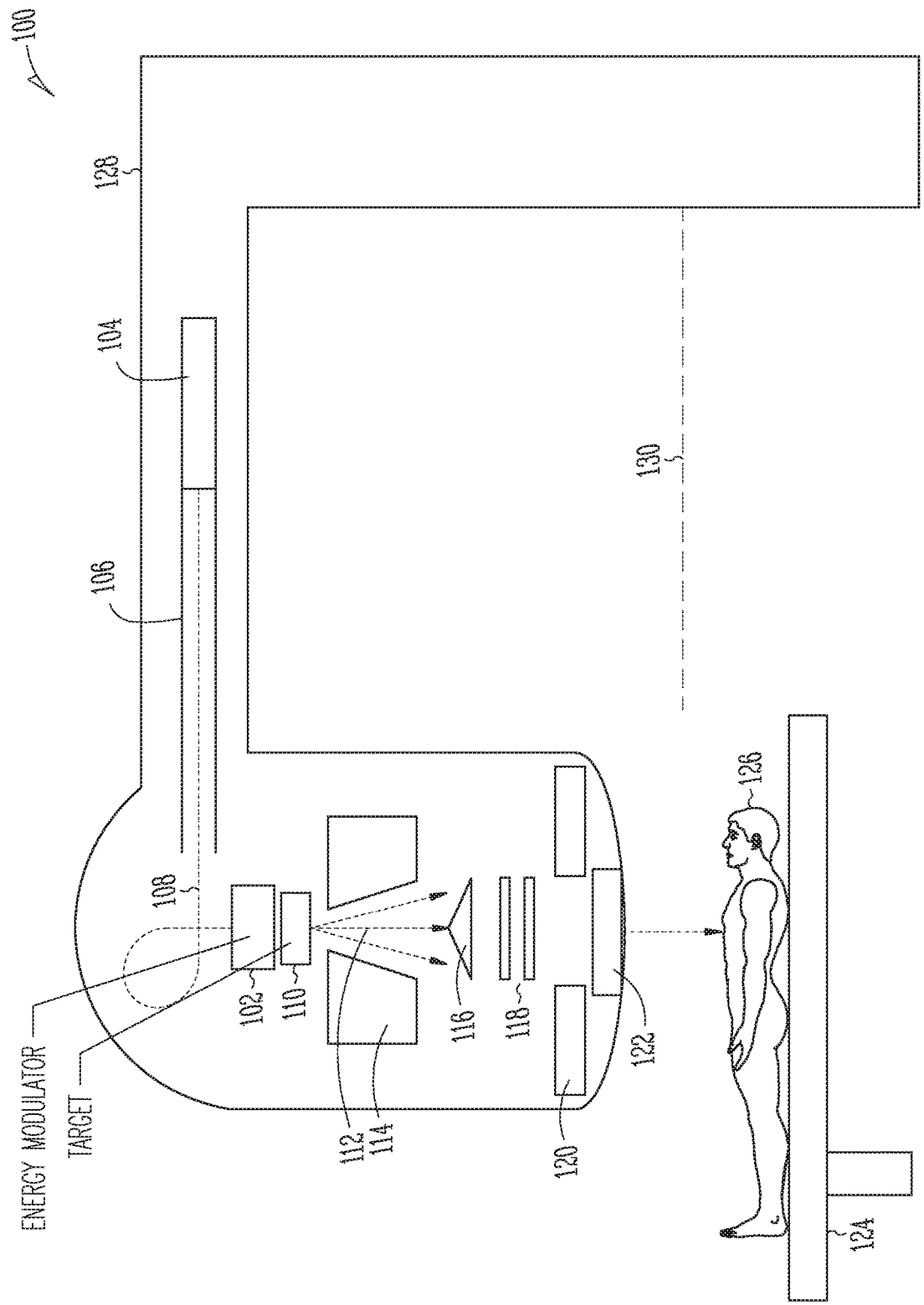
FIG. 1 is a schematic diagram of an example x-ray radiation therapy system in accordance with various embodiments.

FIG. 1 schematically illustrates an example x-ray radiotherapy system 100 in accordance with various embodiments. The system 100 includes a medical LINAC, e.g., as known to those of ordinary skill in the art, retrofitted with an electron-energy modulator (conceptually indicated at 102) upstream of the x-ray converter target or, alternatively, with a combined energy-modulating x-ray converter target in place of a conventional x-ray converter target. The LINAC includes an electron gun 104 or other electron injection system, and an accelerator that includes an accelerator waveguide 106 and is driven by a radio-frequency (RF) power source (not shown), in which the electrons are accelerated to MeV energies. Medical LINACs commonly create more or less monoenergetic electron beams 108 with electron energies between about 4 MeV and about 25 MeV (depending on the length of the accelerator waveguide 106); standard energies include, e.g., 6 MeV, 9 MeV, 12 MeV, 16 MeV, and 18 MeV.

When the electrons hit a target of suitable material, they generate, in the course of being slowed down by interactions with the target atoms, x-rays 112 (primarily Bremsstrahlung); the target 110 is therefore also referred to as the x-ray converter target. The efficiency of x-ray generation (i.e., the fraction of electron energy converted into x-rays rather than heat) is a function of the electron energy and the atomic number Z of the target material, with high-Z materials generally achieving higher yields. A suitable and commonly used material for LINAC x-ray converter targets 110 is tungsten, but other metals (including, e.g., mercury) as well as non-metals (such as, e.g., diamond, carbon, water, lithium compounds, or beryllium compounds) may also be used. The generated x-rays 112 have a broad spectral energy distribution with photon energies up to and including the energy of the incident electrons, and with a mean energy (also referred to as the "effective energy" of the x-ray photons) amounting to about one third of that maximum energy. By convention, the spectral energy distribution of an x-ray beam is labeled with the accelerating voltage used for an electron beam generating that spectral distribution. For example, an x-ray beam generated by 6 MeV electrons (and having a mean photon energy of about 2 MeV) would be called a 6 MV x-ray beam.

In accordance with various embodiments, the spectral energy distribution of the x-ray beam 112 is modified by controllably reducing the energy of the electron beam 108 with an add-on electron-energy modulator 102 (or an energy-modulating layer of an integrated energy-modulating x-ray converter target module 102/110) located somewhere in the path of the electron beam. Various example implementations of such an electron-energy modulator and/or associated target modifications are described below with respect to FIGS. 4-8. Using electron-energy modulation as described herein, a LINAC ordinarily producing, e.g., 6 MV x-ray beams can generate lower-energy x-rays, e.g., x-rays characterized by spectral energy distributions with maximum energies less than 4 MeV, or less than 1 MeV in some embodiments. This capability closes a gap in existing x-ray-generating technologies, where high-output, reliable x-ray sources particularly in the mid-energy range (between about 1 MV and about 4 MV) are difficult to find.

With renewed reference to FIG. 1, due to spatial constraints imposed in application settings, it is often not possible to align the accelerator waveguide 106 with the direction of incidence of the electron beam 108 onto the x-ray converter target 110. Therefore, the LINAC may further include a beam transport system. e.g., implemented by magnets, for redirecting the electron beam that leaves the accelerator 104 onto the target 110. In many medical LINACs, as shown, the electron-beam direction is altered by 90° from horizontal to vertical.

The LINAC further includes an x-ray beam collimation and monitoring system, which may, e.g., include a primary collimator 114 that defines a maximum circular field of the x-ray beam, a flattening filter 116 for generating a uniform intensity distribution over the collimated field, a monitoring chamber (e.g., an ionization chamber) for measuring the photon (and any remaining electron) output and x-ray beam flatness, and a secondary collimator 120 for generating, e.g., a rectangular field. In IMRT applications, the LINAC may further be equipped with an MLC 122 (or multiple MLCs arranged in series), which usually contain tens (in some cases over a hundred) of individually controllable, motorized collimator "leaves" that can move in and out of the x-ray beam path to form small apertures that, collectively, shape the beam and/or, by transiently blocking portions of the beam, control the intensity (or, more precisely, fluence) distribution of the beam. As illustrated in and explained with respect to FIGS. 10-11D, the MLC 122 may also serve, in accordance with some embodiment, to monitor the intensity and spectral energy of the x-ray beam, simultaneously with shaping the beam.

The radiotherapy system 100 may further include a treatment table (or treatment couch) 124, on which a patient 126 may be positioned for x-ray treatment. LINAC components including at least the x-ray converter target 110 and x-ray beam collimation and monitoring system downstream thereof (collectively the "x-ray source") may be mounted in a gantry 128 that can rotate about a (horizontal) gantry axis 130 to irradiate the treatment target in the patient 126 from different angles. In some embodiments, a full 360° rotation is possible. (Other LINAC components, such as the electron gun 104, accelerator waveguide 106, and/or RF power source, may be located in the gantry or, alternatively, in a separate, fixed stand, from which the electrons can be transported into the gantry by a suitable beam transport system.) The gantry 128 may also allow tilting the x-ray beam (e.g., via independent movement of a treatment head housing the x-ray source) relative to the vertical direction, and/or laterally moving the beam parallel to the gantry axis 130. Alternatively or additionally, the treatment table 124 may be configured to move linearly or rotate underneath the x-ray source.

Figure 13:
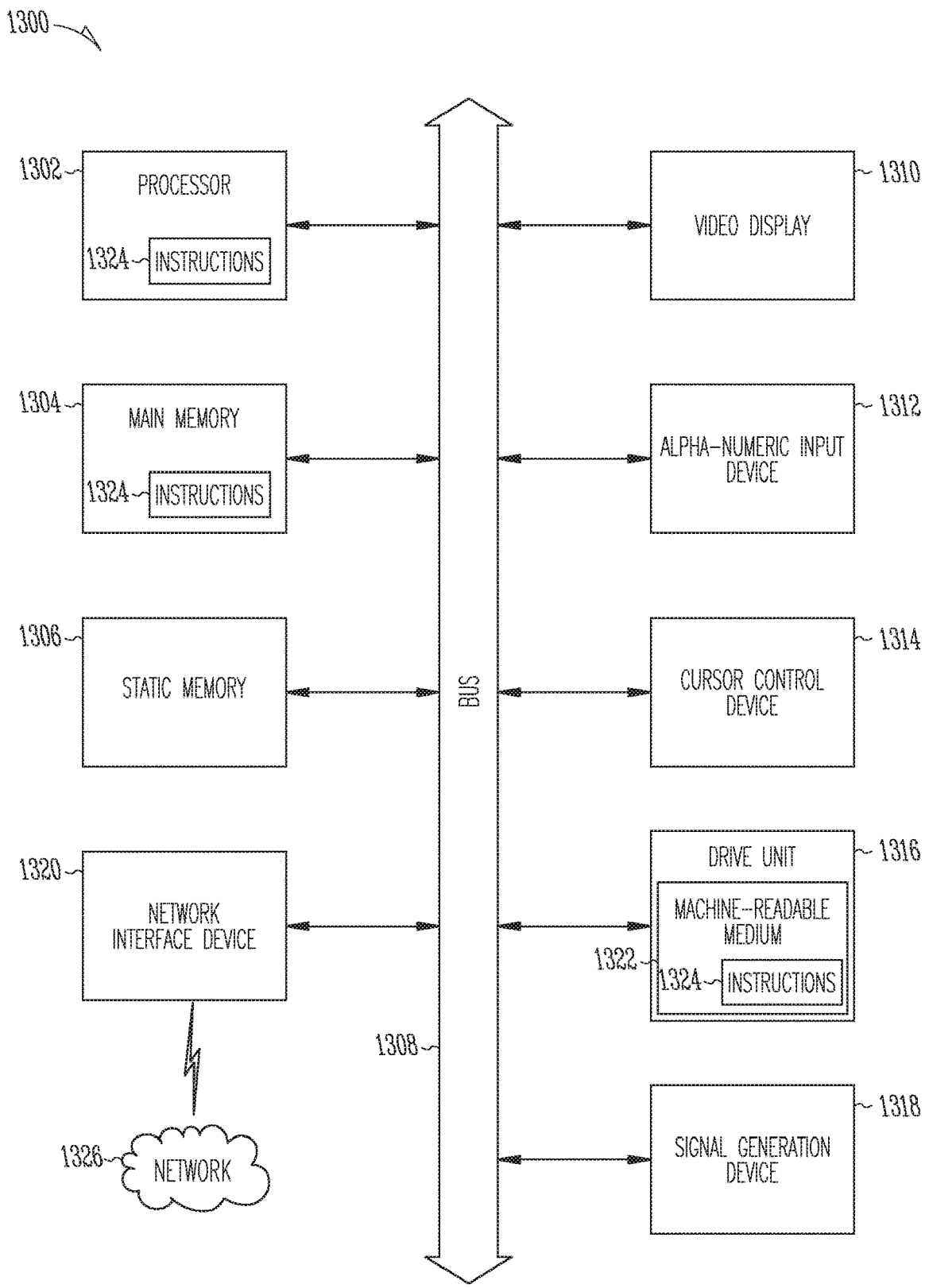
FIG. 13 is a schematic block diagram of an example computing system that may be used for performing treat-

The radiotherapy system 100 further includes a control system (not shown) for controlling the operation of the LINAC, including, in particular, the electron-energy modulator 102 and MLC 122, for energy-modulated IMRT/VMAT. The control system may execute a treatment plan, e.g., computed based on image data (e.g., computerized axial tomography (CAT) scans or magnetic resonance imaging (MRI) data) of a region within the patient that includes the treatment target, to adjust the spectral energy and beam intensity/shape/fluence distribution as the x-ray beam 108 is moved around the treatment target. The control system may be implemented by a suitably programmed computer (e.g., as shown in FIG. 13) or, generally, any suitable combination of hardware and/or software. Computing hardware of the control system may generally include one or more general-purpose or special-purpose processors, such as, e.g., one or more central processing units (CPUs), graphic processing units (GPUs), application-specific integrated circuits (ASICs), field-programmable gate arrays (FPGAs), or digital signal processors (DSPs).

Figure 2:
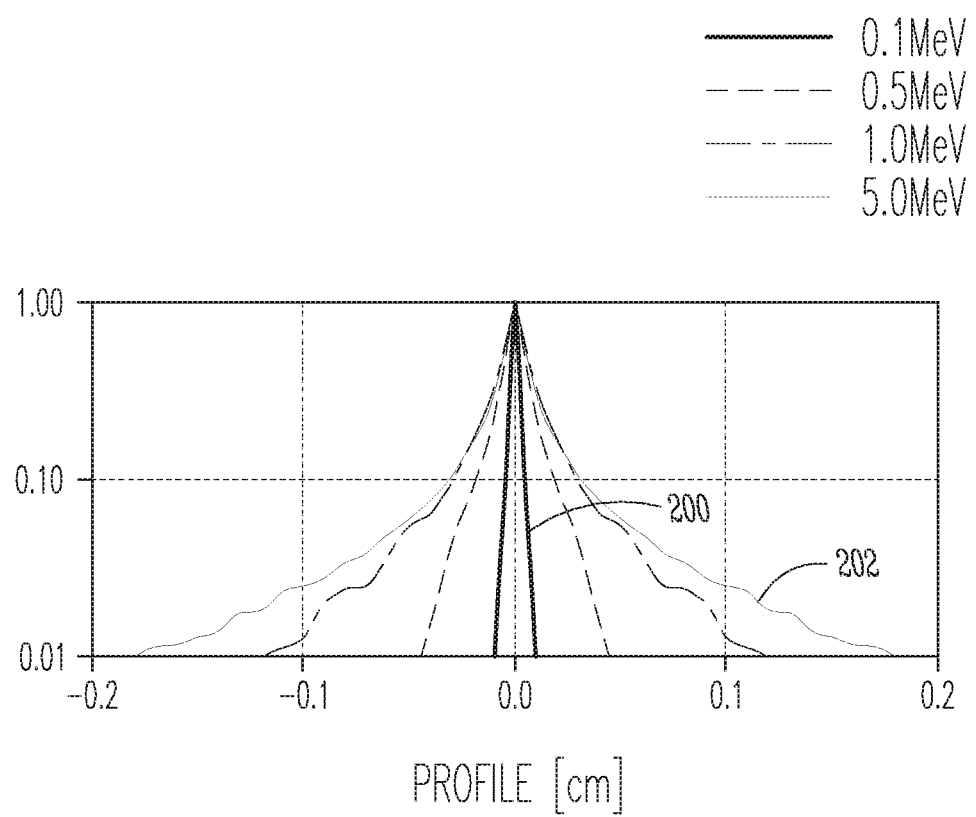
FIG. 2 is a graph of example cross-sectional dose profiles for various x-ray photon energies at a specified target depth, illustrating the dependence of dose gradients on photon energy.
Figure 3B:
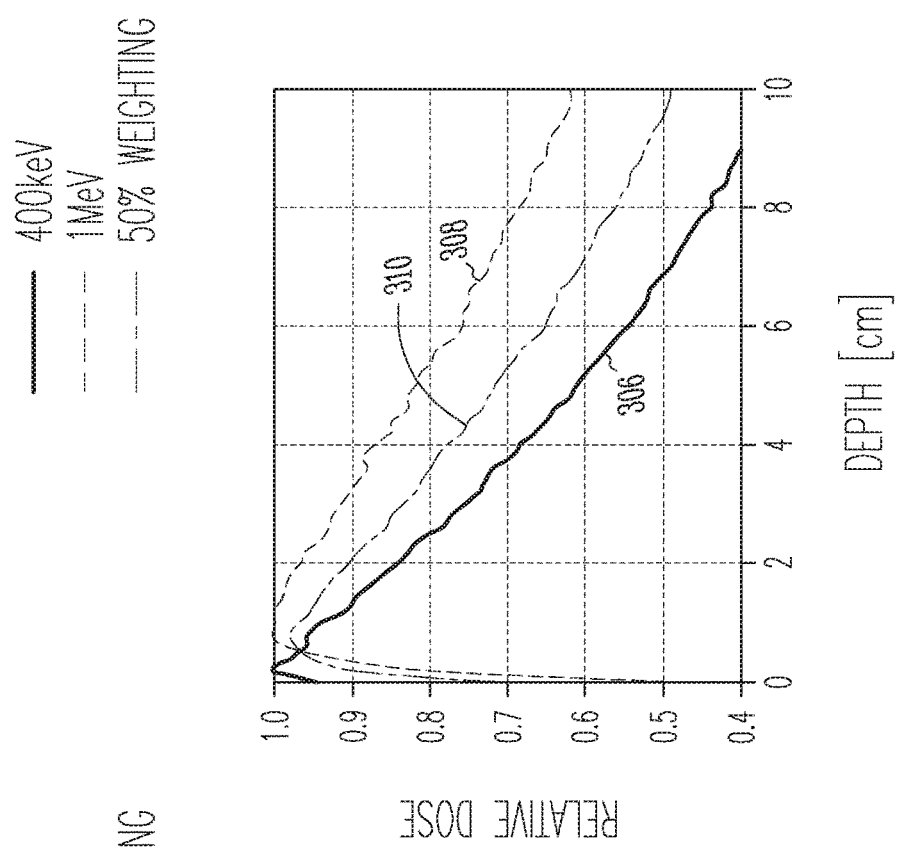
FIGS. 3A and 3B are graphs of cross-sectional and depth dose profiles, respectively, for two x-ray photon energies as well as a weighted mixture thereof, illustrating the trade-off between penetration and penumbra.

In accordance with various embodiments, the spectral energy of the therapeutic x-ray beam and, optionally, the shape of the radiation field and/or fluence distribution created, e.g., by an MLC are adjusted during treatment to create steep dose gradients between the high-dose region (e.g., the tumor) and the low-dose region (e.g., the surrounding normal tissues). The steeper the dose gradient, the greater is the potential to spare normal tissues and sensitive structures (e.g., the spinal cord, optic chiasm, or brain stem) and to escalate the tumoricidal dose. The dose gradients achievable by a LINAC depend in part on the geometry of the MLC, but are also subject to a fundamental physical limit, corresponding to the spectral energy of the x-rays, beyond which further mechanical improvements to the MLC have little effect on increasing dose gradients. This limitation on producing large gradients is mainly due to the trade-off between the x-rays' ability to penetrate tissue vs. the range and trajectory of secondary electrons produced from Compton-scattering interactions. High-energy x-rays have deeper penetration, whereas lower-energy x-rays produce steeper gradients. From a physics perspective, this is because, at a lower energy (e.g., in the keV range), x-ray interactions are dominated by the photoelectric effect, where the interacting x-ray photon is absorbed and the dose does not spread beyond the point of interaction, creating high dose gradients. For higher-energy x-rays (e.g., in the MeV range), on the other hand, interactions are dominated by Compton scattering, which spreads a portion of the incident x-ray energy away from the point of interaction, degrading the dose gradient. FIGS. 2-3B further illustrate the trade-off between penetration and dose gradients.

FIG. 2 shows example cross-sectional dose profiles computed (my Monte-Carlo simulation) for various photon energies ranging from 0.1 MeV to 5 MeV at a target depth of 5 cm in water (as an approximation of biological tissue). The depth is measured from the point where the x-rays impinge on the water. Along the abscissa, the lateral distance from the beam axis is indicated. As can be seen, 0.1 MeV x-rays spread only slightly over the 5 cm range, generating a sharply peaked dose distribution 200 with a width of about 0.02 cm. With increasing x-ray energy, the spread increases, reaching, at 5 MeV, a width of the dose distribution 202 of about 0.4 cm, with a much larger fraction of the dose farther away from the dose peak at the beam axis. With an x-ray beam shaped to conform to a given treatment target, these softer dose gradients generate a substantial "penumbra" around the edges of the target. The penumbra is generally defined as the region between iso-dose lines corresponding to, e.g., 80% and 20%, respectively, of the target dose. As FIG. 2 illustrates, lower x-ray energies tend to result in sharper penumbras.

Figure 3A:
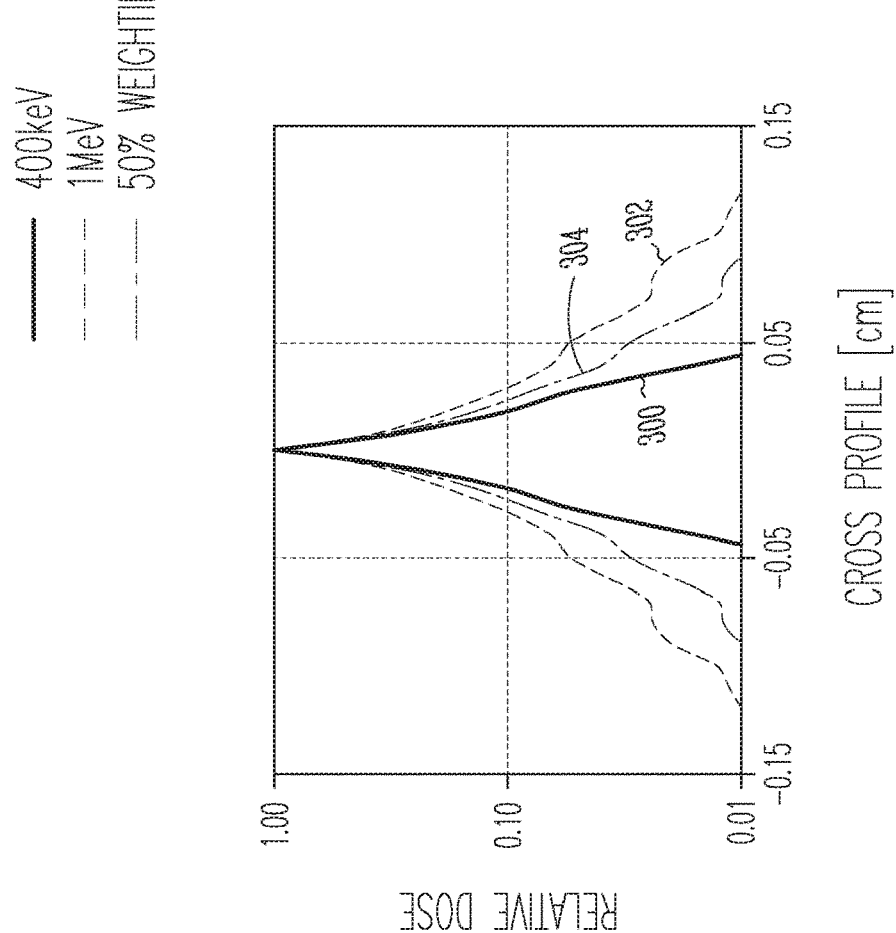

FIG. 3A shows simulated cross-sectional dose profiles 300, 302, 304 for two monoenergetic x-ray beams with photon energies of 400 keV (profile 300) and 1 MeV (profile 302), respectively, as well as for a beam that includes both photon energies in a 50% weighting (i.e., 1:1 ratio) (profile 304). As can be seen, the dose gradient and penumbra of the mixed-energy beam are somewhere in between those of the lower- and higher-energy beams. FIG. 3B illustrates the simulated depth dose profiles 306, 308, 310 (i.e., dose profiles along the path of the x-ray beam) for the lower-energy, higher-energy, and mixed-energy beams, respectively. As shown, the dose peaks shortly after the entry point at which the x-rays impinge on the water, and then gradually falls off with increasing depth. For higher photon energies, the dose decreases more slowly with depth. Thus, higher-energy x-ray beams deposit a larger fraction of their energy at greater depths, i.e., exhibit deeper penetration. Furthermore, the dose peak moves farther away from the entry point, such that less energy is absorbed at the surface. In the radiotherapy context, this effect is also called the "skin sparing" effect. In summary, the benefits of using x-rays with high spectral energies (e.g., megavoltage x-rays) in cancer therapy are increased penetration for treating deep-seated tumors and the ability to take advantage of skin sparing effects. X-rays with low spectral energies (e.g., kilovoltage x-rays), on the other hand, enable steeper dose gradients. In practice, the advantage of skin sparing effects is diminished as the number of angles from which the target is treated increases. Thus, for VMAT, it becomes feasible to utilize lower spectral energies without risking damage to the patient's skin (or other tissue boundaries). Turning now to FIGS. 4-8, various example embodiments of an electron-energy modulator 102 or energy-modulating x-ray converter target module 102/110 are described.

FIG. 4 is a schematic diagram of an example energy-modulating x-ray converter target module 400 that includes an x-ray converter target layer 402 (e.g., a conventional tungsten target) enclosed within a liquid-filled moderator chamber (or housing) 404. In various example embodiments, the liquid is water, although other liquids, such as liquid nitrogen, mercury, bromine, Cerrobend, or solutions with high concentration of high-atomic-number chemicals like sodium iodine, may also be used. The liquid slows down the high-energy electrons 406 entering the moderator chamber 404, thereby lowering the energy of the electrons that ultimately hit the x-ray converter target layer 402. In other words, the liquid forms an energy-modulation layer 408 above the target layer 402, defined between the upper surface of the target layer 402 and the upper interior surface of the chamber 404. The thickness of this energy-modulation layer 408 can be adjusted, in accordance with various embodiments, by moving the target layer 402 in the direction of the impinging electron beam (corresponding to the vertical direction in FIG. 4), e.g., using adjustment pins 410 as shown, a rotating shaft that slides the target along stationary pins or some other mechanism. Suitable mechanisms will occur to those of ordinary skill in the art. As the thickness of the energy-modulation layer 408 is varied, the electron energies incident on the target layer 402 and, as a result, the spectral energy distribution of the x-rays 412 generated in the target layer 402, also varies. As will be appreciated by those of ordinary skill in the art, the energy-modulating x-ray converter target module 400 provides a straightforward means to dynamically adjust the x-ray spectral energy distribution (e.g., as characterized by its mean or maximum energies) along a continuous energy range.

In addition to moderating the electron energies, the water (or other liquid) filling the moderator chamber 404 simultaneously fulfills another purpose: to cool the x-ray converter target 402. Cooling becomes more important at lower electron energies, as the efficiency of x-ray generation decreases, and the amount of heat generated in the target, accordingly, increases, towards lower electron energies. Without cooling, the electron fluxes customarily generated in LINACs, in conjunction with lower electron energies as achieved in accordance herewith, may cause the target to melt. In the energy-modulating x-ray converter target module 400 shown in FIG. 4, continuous heat dissipation is provided by flowing the water (or other cooling liquid) constantly across the x-ray converter target layer 402 via a flow entrance 414 and exit 416.

Figure 5A:
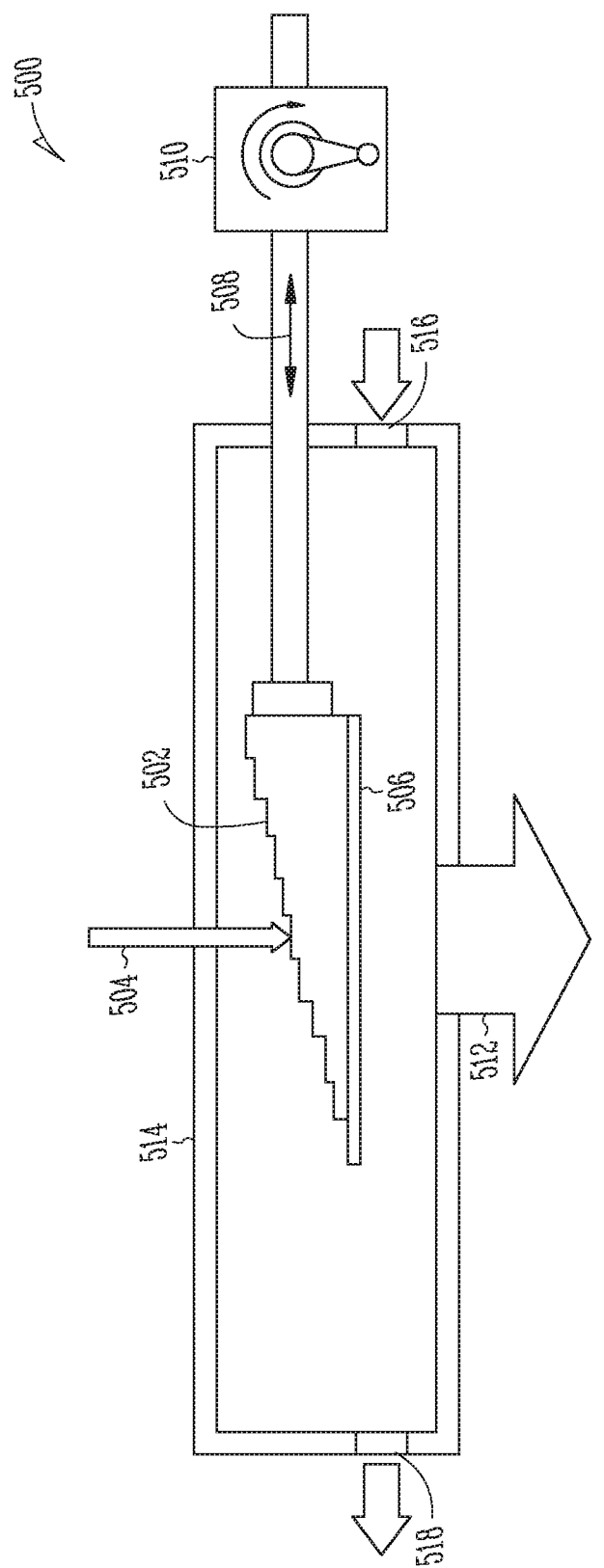
FIG. 5A is a schematic diagram of an example energy-modulating x-ray converter target module including an energy-modulating layer varying in thickness in a direction perpendicular to an impinging electron beam, in accordance with various embodiments.

FIG. 5A is a schematic diagram of an example energy-modulating x-ray converter target module 500 that includes an energy-modulating layer 502 varying in thickness in a direction perpendicular to the impinging electron beam 504 (corresponding to the horizontal direction in FIG. 5A), in accordance with various embodiments. The energy-modulating layer 502 may be made, e.g., of copper, aluminum, diamond, graphite, or some other suitable moderator material, and serves to slow down the electrons 504 before they hit the x-ray converter target layer 506. Criteria for selecting moderator materials include the capability of a material to maintain its integrity under extreme heat during operation as well as the atomic number of the material, which is preferably low to reduce the amount of x-rays produced as the electrons pass through the material. As shown, the energy-modulating layer 502 may take the general shape of a wedge. The slanted surface of the wedge may be "stepped" such that the thickness of the energy-modulating layer 502 increases in discrete steps (e.g., at constant increments) in the lateral direction (i.e., perpendicularly to the electron beam). Alternatively, the slanted surface may be smooth for a continuous thickness variation. The thickness of the energy-modulating layer 502 may vary linearly in the lateral direction, or have some other functional dependence resulting, e.g., in a curved wedge surface. The energy-modulating layer 502 is movable relative to the electron beam 504 (and either relative to the target layer 506 or along with the target layer 506) in the lateral direction, e.g., by a piston 508 driven by a rotating shaft 510, or by some other mechanism. Suitable mechanisms will occur to those of ordinary skill in the art. As the energy-modulating layer 502 is moved perpendicularly to the electron beam 504, the thickness encountered by the electron beam 504 is varied, causing the electrons to be slowed down to varying degrees, and shifting the spectral energy distribution of the x-rays 512 generated in the adjacent x-ray converter target layer 506 accordingly. (The target layer 506 may, but need not necessarily, be directly adjacent the converter target layer 506. It is also possible to keep the two layers 502, 506 at some mutual distance.) Thus, like the embodiment of FIG. 4, the energy-modulating x-ray converter target module 500 of FIG. 5 enables dynamic and continuous adjustments of the x-ray spectral energy distribution.

For purposes of cooling the target layer 506, the energy-modulating and x-ray converter target layers 502, 506 may be enclosed in a housing or chamber 514, and a cooling liquid such as water may be flown through the chamber 514 (entering at 516 and leaving at 518) and across the target layer 506 (and energy-modulating layer 502). Note that, although the water above the target layer 506 contributes to the reduction in electron energy, the energy reduction per unit length penetrated differs between the water and the moderator material of the energy-modulating layer 502, providing a net difference in electron-energy reduction that depends on the thickness of the energy-modulating layer 502 encountered by the electron beam 504.

Figure 5B:
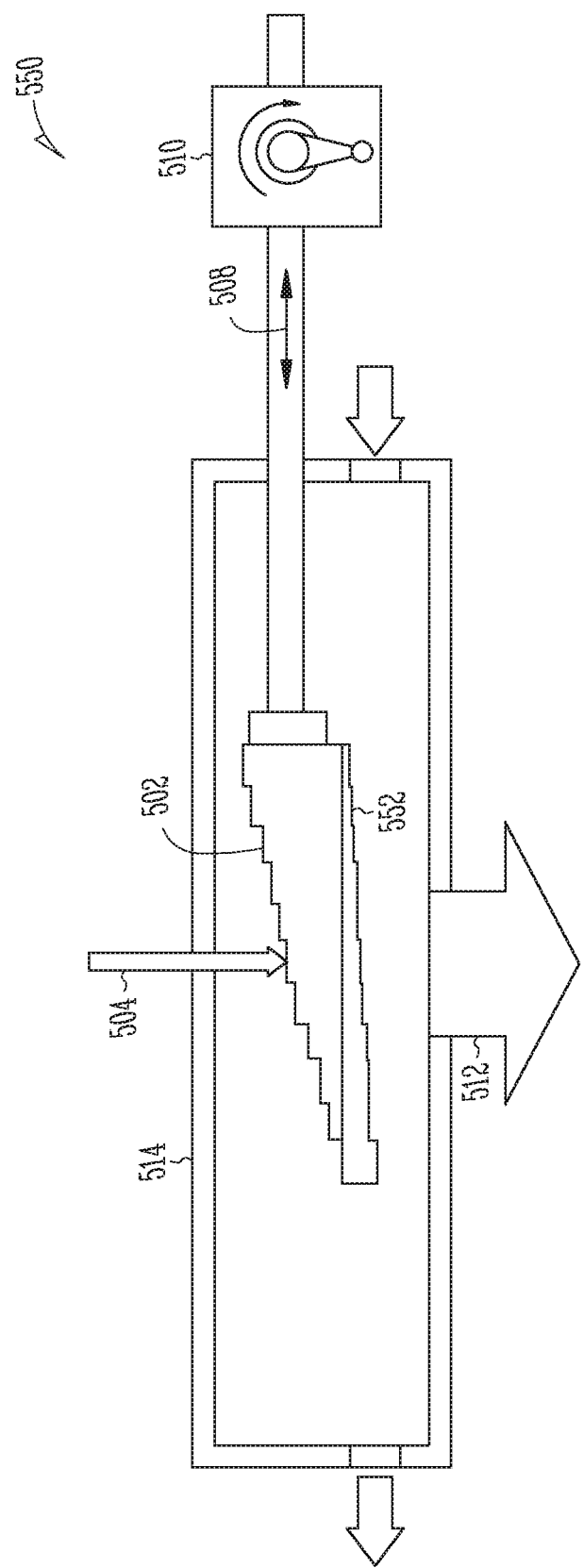
FIG. 5B is a schematic diagram of an example energy-modulating x-ray converter target module including energy-modulating and converter target layers each varying in thickness in a direction perpendicular to an impinging electron beam, in accordance with various embodiments.

FIG. 5B is a schematic diagram of an example energy-modulating x-ray converter target module 550 that, as a variation of the above-described module 500, has energy-modulating and converter target layers 502, 552 both varying in thickness in a direction perpendicular to the impinging electron beam 504, in accordance with various embodiments. As shown, the variable-thickness x-ray converter target layer 552 may be wedge-shaped, optionally with a stepped slanted surface, like the energy-modulating layer 502. The two layers 502, 552 may be joined at their respective unslanted surfaces, and may be moved together (e.g., by the piston 508). The x-ray converter target layer 552 may be oriented such that its thickness increases in the opposite direction as the thickness of the energy-modulating layer 502. This configuration may serve to ensure that the higher-energy electrons that exit the energy-modulating layer 502 at the thinner end are fully absorbed in the target layer 552 at its correspondingly thicker end, while the lower-energy electrons exiting the energy-modulating layer 502 at the thicker end encounter a thinner portion of the target layer 552 such that the target thickness through which the generated x-rays have to go is minimized. Additionally, the x-rays generated in the x-ray converter target layer 552 are filtered in the remainder of the target layer 552, with lower energy x-rays being absorbed by the material; as a result, the effective energy of the beam increases with increasing thickness of the x-ray converter target layer 552.

Figure 6:
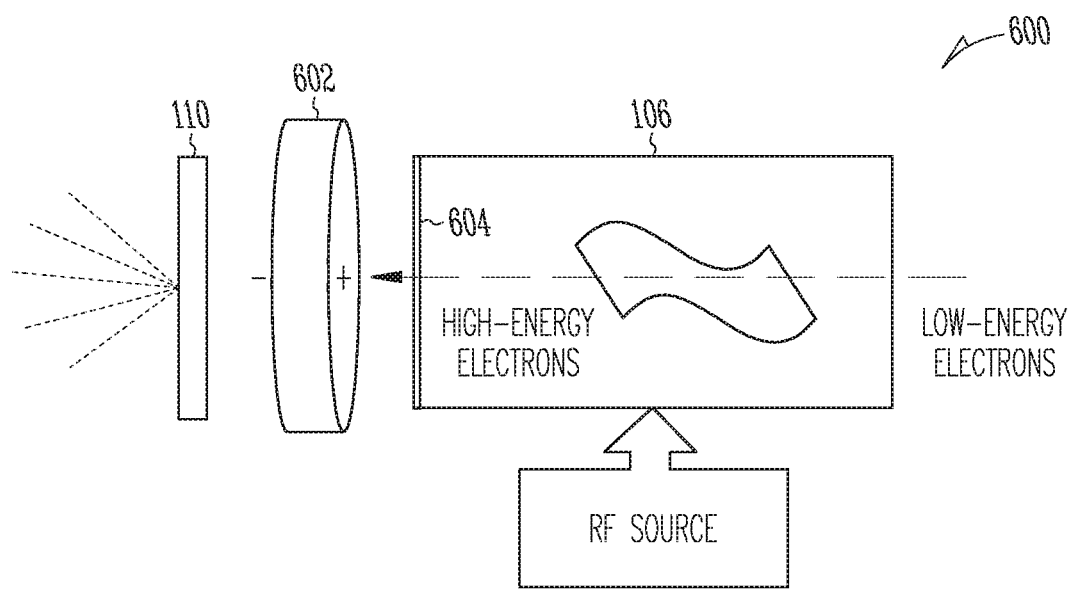
FIG. 6 is a schematic diagram of an example energy-modulating linear accelerator system that employs a variable electric field to reduce the energy of the electron beam prior to x-ray generation, in accordance with various embodiments.
Figure 7:
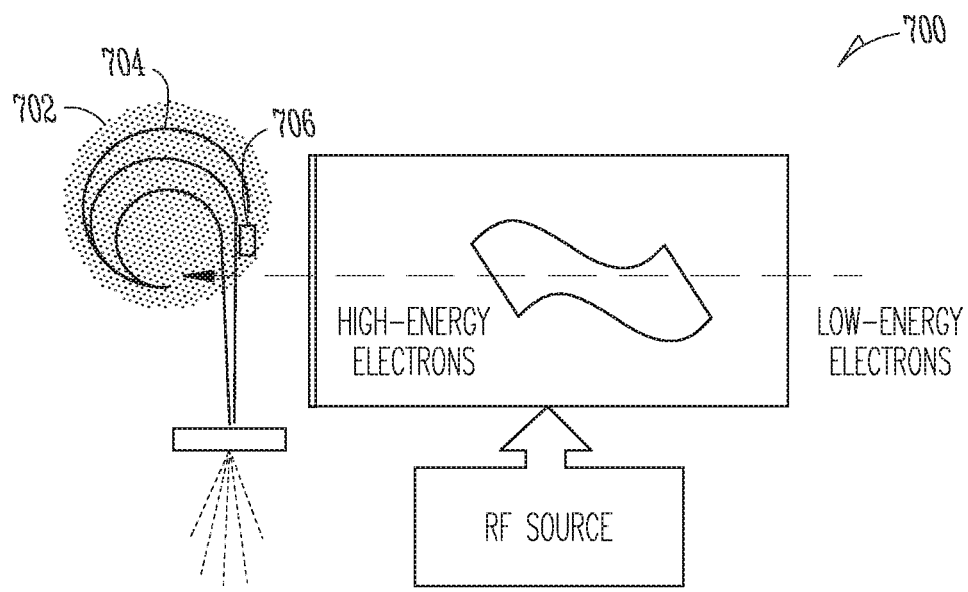
FIG. 7 is a schematic diagram of an example energy-modulating linear accelerator system that selectively absorbs high-energy electrons to modulate the spectral energy distribution of the electron beam prior to x-ray generation, in accordance with various embodiments.

FIGS. 4-5B describe various modules that combine functionality for electron-energy modulation and x-ray generation and that may, thus, replace the conventional x-ray converter target in a LINAC. FIGS. 6 and 7, by contrast, describe alternative approaches to modulating the energy of the electron beam that utilize add-on components placed in the LINAC upstream of a conventional x-ray converter target.

FIG. 6 is a schematic diagram of an example energy-modulating linear accelerator system 600 that employs a variable electric field to reduce the energy of the electron beam prior to x-ray generation, in accordance with various embodiments. This field, conceptually depicted at 602, is placed in the electron beam path somewhere between the exit window 604 of the accelerator waveguide 106 and the x-ray converter target 110 (shown as arranged along a common axis merely for simplicity), and is oriented such that the field lines (from the plus pole to the minus pole) point in the same direction in which the electrons move. The electric field 602 may be generated by a suitable arrangement of electrodes (e.g., capacitor plates) connected to a high-voltage source. The voltage source may, for instance, apply voltages between 2 MV and 5 MV to reduce the electron energy from, e.g., initially 6 MeV to a range from 1 MeV to 4 MeV. The voltage may be continuously tunable within a given range, enabling the x-ray spectral energy distribution to be likewise continuously shifted in energy. To avoid spatial spreading of the electron beam in the electric-field configuration, the system 600 may further include one or more electromagnetic lenses or other suitable inductor configurations generating magnetic fields for refocusing the beam.

FIG. 7 is a schematic diagram of an example energy-modulating linear accelerator system 700 that selectively absorbs high-energy electrons to modulate the spectral energy distribution of the electron beam prior to x-ray generation, in accordance with various embodiments. Ordinarily, the linear accelerator is optimized for electron beams as close as monoenergetic as possible. In the embodiment of FIG. 7, however, the linear-accelerator configuration may be deliberately altered to degrade its energy-focusing properties and produce a broader electron-energy distribution. As the electrons are redirected in a magnetic field 702 of the beam transport system, they will be spread out by energy, as faster electrons follow trajectories 704 with larger radii than slower electrons. This spatial spreading of energies can be exploited to modify the electron-energy distribution by selectively filtering out, e.g., the faster electrons, thereby shifting the average energy of the electron beam to lower energies. The filtering can be achieved, e.g., by placing electron absorbers 706 (e.g., blocks of plastic, containers filled with water, or other materials with low atomic number) in the field to physically block portions of the electron beam, or by shielding a portion of the magnetic field to allow electrons within the desired filtered energy range to exit the device.

Figure 8:
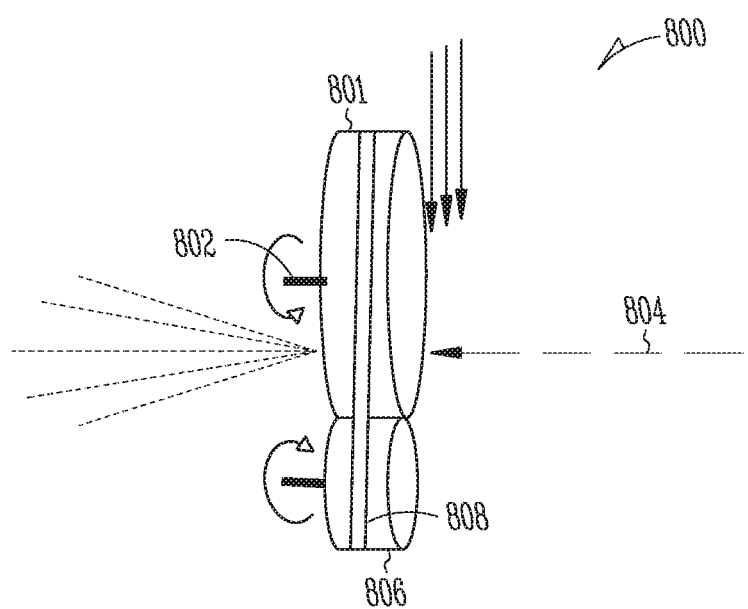
FIG. 8 is a schematic diagram of an example rotating x-ray converter target for improved heat dissipation, in accordance with various embodiments.

FIG. 8 is a schematic diagram of an example rotating x-ray converter target configuration 800 for improved heat dissipation, in accordance with various embodiments, as may be used, e.g., in conjunction with the electron-energy-reducing approaches illustrated in FIGS. 6 and 7. As noted above, the use of lower electron energies increases the amount of heat generated in the x-ray converter target. To avoid the target from burning through, a cooling liquid may be flowed past the target. Alternatively or additionally, as shown in FIG. 8, the target 801 may be rotated about an axis 802 parallel to, but displaced from, the axis 804 along which the electron beam is incident upon the target 801, such that different areas of the target are hit at different times (e.g., periodically), allowing the target 801 to cool in between repeated encounters of the same target area by the electron beam. In some embodiments, the target 801 takes the shape of a circular disk whose rim is placed in mechanical contact with a motorized rotating disk 806, optionally with a belt 808 surrounding both disks 801, 806 to assist in mechanically transferring the rotation of the motorized disk 806 to the target 801.

The x-ray radiotherapy system 100 of FIG. 1, in conjunction with one or more of the devices and configurations of FIGS. 4-8, or with other means for modulating the spectral energy distribution of the x-ray beam, can be used, in accordance with various embodiments, to deliver energy-modulated radiation to a treatment target. The therapy may include irradiating the treatment target from multiple angles, and the x-ray spectral energy distribution may vary in part based on the angle. Alternatively or addition, the therapy may involve blending, at one or more angular positions, two or more spectral energy distributions (with different respective maximum energies). Blending can be achieved by sequentially irradiating the target with different x-ray spectral energy distributions. In some embodiments, energy modulation involves making a selection between two, or a few, discrete spectral energy distributions, such as, e.g., between a 6 MV beam and a 2 MV beam. In other embodiments, the spectral energy distribution can be selected from a continuum or quasi-continuum (i.e., a large number of distributions with very finely spaced maximum or mean energies), e.g., the range between 1.2 MV beams and 6 MV beams (corresponding to average photon energies of from about 400 keV to about 2 MeV).

Variation of the spectral energy distribution of the x-ray beam may go hand in hand with variation of the beam shape, intensity, and/or intensity distribution (across the cross-sectional beam profile). In some embodiments, the beam shape and intensity distribution are manipulated using an MLC, which enables subdividing each radiation beam into smaller radiation beamlets and varying the individual intensities of these beamlets. The movable leaves of the MLC can be configured to selectively block or transmit each beamlet, thereby configuring the shape of the beam, as well as to only transiently block each beamlet for variable amounts of time, thereby controlling the aggregated fluence or average intensity of radiation for the beamlet over a unit of time. As the target is irradiated from a given angle, the MLC may undergo a sequence of configurations that collectively achieve a prescribed intensity distribution, with specified intensities for the individual beamlets. In addition, the spectral energy distribution of the x-rays may be varied between respective configurations, providing flexibility to control the weighting between multiple spectral energy distributions in a blended spectral energy distribution independently for each individual beamlet. The treatment can be delivered in static or dynamic modes, which differ in whether irradiation is stopped (i.e., the beam is turned off) in between reconfigurations (of the beam intensity distribution, spectral energy distribution, or angular position of the beam relative to the target), or whether the target is continuously irradiated as the beam is changed and/or moves around the target. In various embodiments, energy modulation is used as an enhancement of VMAT, whereby the x-ray spectral energy distribution is changed dynamically as the beam is moved around the target in an arc.

Alternatively to modifying the spectral energy distribution of a single x-ray beam, energy blending can also be achieved, in accordance with some embodiments, by using two or more separate x-ray beams created in a therapy system including multiple x-ray sources in multiple respective treatment heads (the treatment head being the portion of the gantry housing the x-ray source). The multiple beams may simultaneously irradiate the treatment target from different angles and may, as the gantry rotates, cover different respective arcs. At some point, however, the arcs will overlap, reaching 100% mutual overlap after a complete rotation. Thus, aggregating the radiation dose received from each given angle over time, the x-ray spectra of the multiple beams can be blended at any given angular position.

Figure 9:
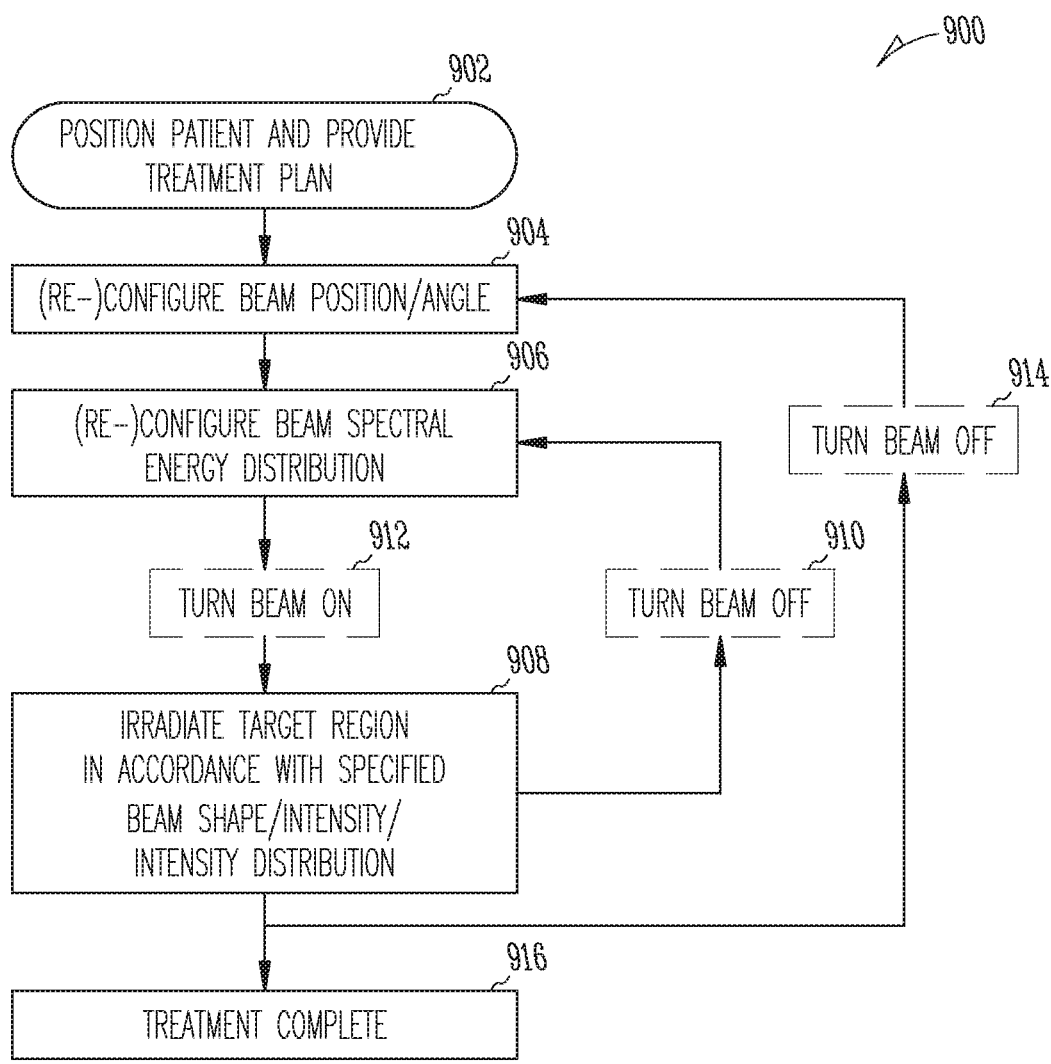
FIG. 9 is a flow chart of an example method for energy-modulated radiation therapy in accordance with various embodiments.

FIG. 9 is a flow chart of an example method 900 for energy-modulated radiation therapy in accordance with various embodiments, as may be performed with a LINAC system such as system 100 shown in FIG. 1. Starting point 902 of the method 900 is a patient (e.g., 126) positioned for treatment on the treatment couch (e.g., 124), along with a treatment plan for a given target within the patient. The treatment plan specifies the spectral energy distributions and intensities for the beam or beamlets for each angular position, and may be computed, e.g., in accordance with the method of FIG. 12 described below.

The treatment method 900 involves moving the x-ray source of the LINAC in position for the desired beam position and angle (e.g., by rotating the gantry of the LINAC to the appropriate rotational position) (act 904). Further, the method 900 includes configuring the LINAC for the x-ray spectral energy distribution specified in the treatment plan, e.g., by controlling the electron energy (act 906). In various embodiments, the desired spectral energy distribution is achieved by configuring an add-on electron-energy modulator, or energy-modulating layer within an energy-modulating x-ray converter target, of the LINAC. For example, using any of the embodiments 400, 500, 550 of FIGS. 4-5B, the electron energy can be reduced to a desired level by moving the x-ray converter target (in 400) or the energy-modulating layer (in 500 or 550) to a position that adjusts the energy-modulating layer (e.g., water or moderator material) to a corresponding thickness. Using the embodiment 600 of FIG. 6, the electron energy can be adjusted via the voltage generating the electron-slowing electric field. In some embodiments, the electron accelerator itself is operable in different modes generating electron beams of multiple different energies, which may achieve the multiple spectral energy distributions used during treatment without any need for a separate component reducing the electron energy; in this case, the x-ray spectral energy distribution may be configured simply by selecting one of the accelerator modes.

For a set beam angle and spectral energy distribution, the target is irradiated in accordance with a beam shape/intensity or intensity distribution (as created by multiple beamlets that may differ in intensity) likewise specified in the treatment plan (act 908), which generally involves configuring the MLC (or other collimators with adjustable apertures) accordingly. A control sequence of the MLC may be specified in the treatment plan, along with or in lieu of the desired shapeintensity or intensity distribution that it creates. To achieve a complex intensity distribution, e.g., with different intensities for different beamlets, the MLC may go through a series of configurations, either in discrete steps or continuously. For discrete configuration changes, the x-ray beam is turned off prior to and turned back on following each reconfiguration of the MLC (e.g., by turning the electron accelerator on and off), whereas, for continuous configuration changes, the beam is kept on as the MLC configuration is adjusted.

To achieve energy blending of x-rays directed at the treatment target from a given angular position, configuration of the x-ray spectral energy distribution (act 906) and irradiation of the target in accordance with a specified beam shape, intensity, and/or intensity distribution (act 908) may be repeated for one or more additional spectral energy distributions. After each irradiation, the beam may be turned off (act 910) before the beam energy is changed (e.g., by switching to another electron accelerator mode), and then turned back on (act 912). Various embodiments, however, enable dynamic changes to the spectral energy distribution (e.g., as achieved by moving or otherwise adjusting an energy-modulating layer, or tuning a decelerating electric field) during continued irradiation of the treatment target.

Further, the spectral energy distribution may be adjusted simultaneously with the beam intensity distribution (that is, acts 906 and 908 may take place at the same time), in some embodiments.

Upon treatment of the target from one angle, the x-ray source may be moved to another rotational position to reconfigure the beam angle (act 904), and treatment may then proceed with irradiation of the target with a spectral energy distribution and beam shape/intensity/intensity distribution specified for the new angle (acts 906, 908). Again, the beam may be, but need not be, turned off (act 914) in between adjustments of the beam angle. In some embodiments, the gantry is rotated continuously to move the beam continuously around the target in an arc (e.g., at a rotational speed specified in the treatment plan and consistent with the desired x-ray dose), and the beam energy and intensity distribution are modulated simultaneously. The adjustment of the beam angle, energy, and intensity distribution, e.g., as achieved by reconfigurations of the gantry, electron-energy modulator, and MLC continue until the treatment session is completed (at 916).

Figure 10:
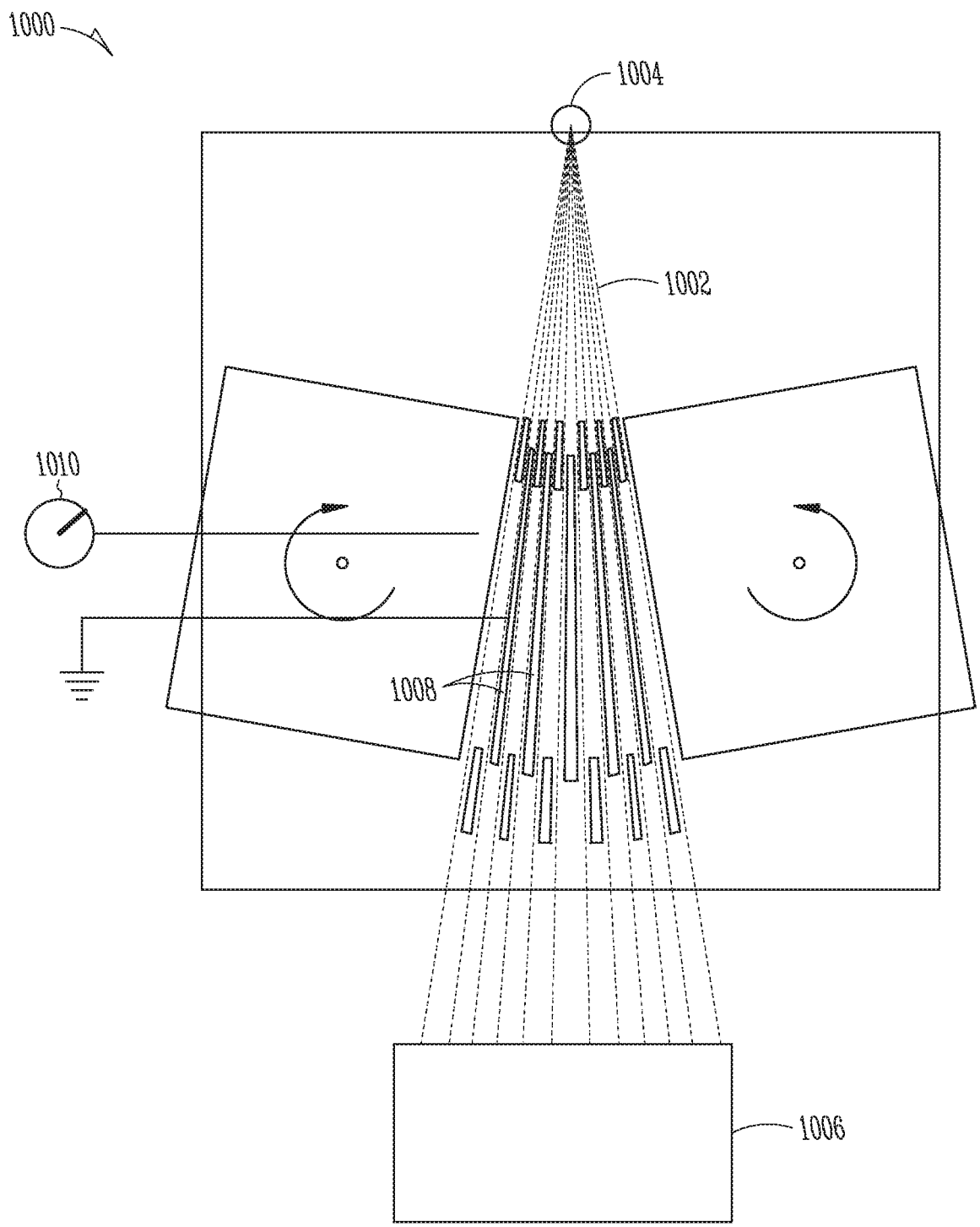
FIG. 10 is a schematic diagram of an MLC used for beam monitoring in accordance with various embodiments.

Energy-modulated radiotherapy (e.g., energy-modulated arc therapy) faces a challenge in monitoring both the spectral beam energy (meaning, in this context, spectral energy distribution as characterized, e.g., by an effective photon energy) and output intensity during operation. In various embodiments, this monitoring capability is provided by the MLC, that is, the MLC acting as the beam collimator/shaper doubles as a device for beam monitoring. With reference to FIG. 10, in an example MLC configuration 1000, shown in top view (with the x-ray beam 1002 extending from the x-ray source 1004 to the treatment target 1006), the MLC (corresponding to MLC 122 in the system 100 depicted in FIG. 1) may include a plurality of leaves 1008 made out of a conducting material (e.g., tungsten). The leaves 1008 (which extend into the plane of the figure) are movable to adjust the spaces between adjacent pairs of leaves 1008, creating a sequence of apertures or slits of variable position and width along the horizontal axis (transverse to the x-ray beam axis). A second MLC (not shown) may be used to define beam apertures along the other dimension transverse to the x-ray beam axis. To use the MLC 1000 for beam-monitoring purposes, it may be configured in pairs, with every other leaf 1008 having a voltage of several hundred volts (and leaves 1008 in between being electrically grounded). The leaves 1008 may be electrically connected to a device that measures small electrical currents, such as an electrometer 1010. The x-rays 1002 that strike the collimator leaves 1008 set in motion electrons that can be collected as a current measured by the electrometer 1010. Each pair of adjacent collimator leaves 1008 thus forms an individual detector (only one such detector being explicitly indicated in the drawing). The strength of the measured signal (i.e., the electric current level) is generally dependent on the volume of cavity between the leaves 1008, the energy of the x-rays 1002 striking the leaves 1008, and the beam intensity.

Figure 11A:
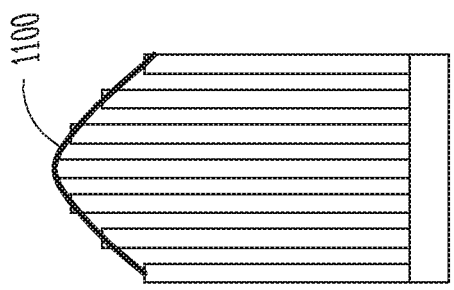
FIGS. 11A-11D are schematic depictions of detector responses of the MLC of FIG. 10 as may be used as indicators of different conditions, in accordance with various embodiments.
Figure 11B:
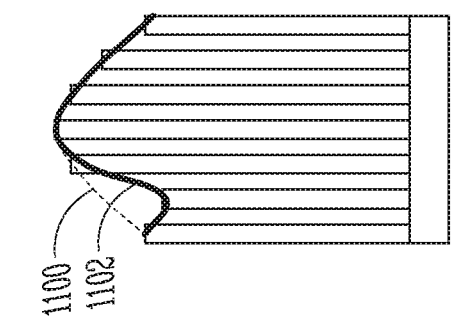
Figure 11C:
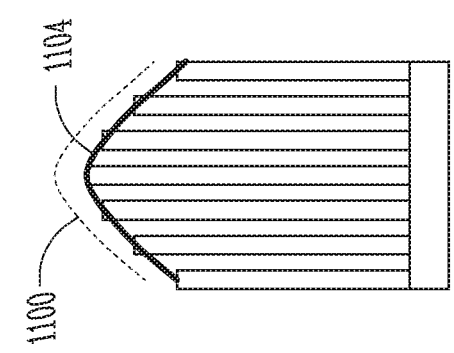
Figure 11D:
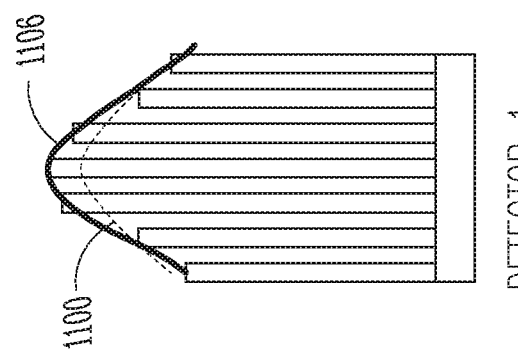

FIGS. 11A-D illustrate detector responses (electrical currents) for n detectors, plotted from detector 1→n (as a bar diagram) to form, in the aggregate, a response curve (obtained by connecting the bars for the individual detectors). From the shape of the response curve as compared with a baseline response curve 1100, which is shown in FIG. 11A, certain x-ray delivery characteristics can be determined: A mechanical defect in the MLC (which becomes more likely with smaller apertures) may be reflected in an abnormal curvature of the response curve 1102, as shown in FIG. 11B. A response curve 1104, similar in shape to the baseline response curve 1100, but shifted in magnitude, as shown in FIG. 11C, may indicate a change in the beam intensity. A sharper response curve 1106, as shown in FIG. 11D, may be an indication of increased spectral energy. Thus, the shape of the response curve can provide valuable information about the cause of a deviation from the baseline. The detector response of the MLC may be connected to safety interlocks to terminate operation of the system if the response curve deviates beyond a tolerance margin from the baseline.

Figure 12:
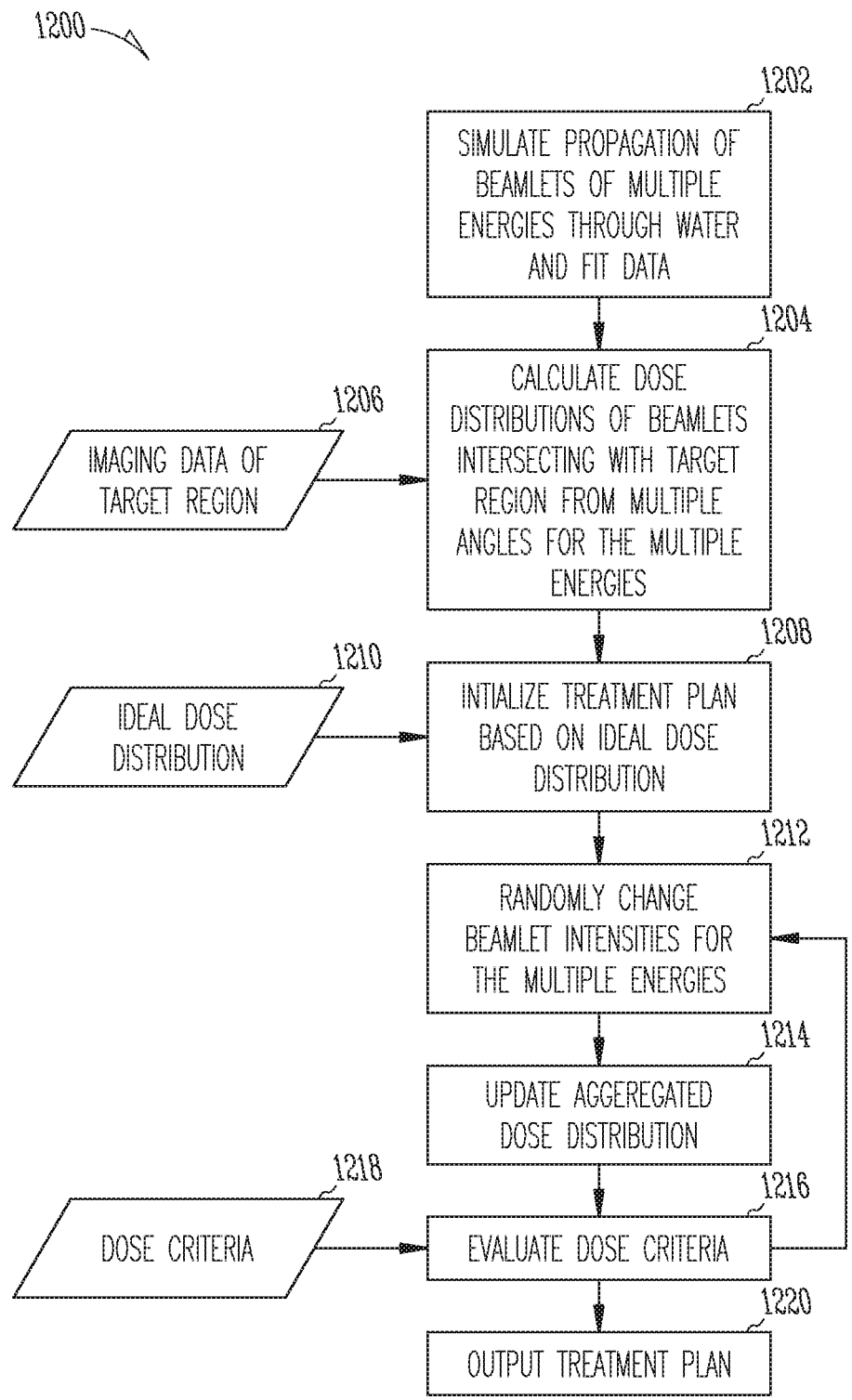
FIG. 12 is a flow chart of an example method for energy-modulated treatment planning in accordance with various embodiments.

With reference now to FIG. 12, an example method 1200 for generating a treatment plan for energy-modulated therapy in accordance with various embodiments is illustrated. The method 1200 may be performed by one or more general-purpose computers executing suitable software, or generally by any suitable combination of computing hardware (including one or more hardware-implemented, general-purpose or special-purpose processors) and/or software. In some embodiments, the treatment-planning method 1200 is implemented in program code (i.e., computer-readable instructions) stored on one or more machine-readable media (e.g., hardware storage devices such as hard disks, CD-ROMs, etc.) and executable by one or more hardware processors.

The example treatment planning method 1200 generates a treatment plan that specifies, for each of a plurality of beam angles, and for each of a plurality of beamlets at each angle, one or more spectral beam energies (meaning, in this context, spectral energy distributions as characterized, e.g., by an effective photon energy) and associated intensities. With two or more fixed spectral beam energies to choose from, the combination of beam energies and intensities may also be described as a weighted combination of beam energies in conjunction with an aggregate intensity. For example, the blending of two spectral beam energies, each delivered with an intensity I, would result in a 50/50 weighting with an aggregate intensity 2I.

The method begins, in act 1202, by simulating the propagation of beamlets of different photon energies or energy distributions through water (chosen as a good approximator for biological tissues), e.g., using Monte Carlo simulation (which is a technique well-known to those of ordinary skill in the art), to determine depth dose profiles associated with the beamlets. The beamlets may be modeled for the full spectral energy distribution of the x-rays that will be delivered in practice, or may, alternatively and for the sake of computational simplification, be modeled as monoenergetic (e.g., using the mean energy to represent a certain spectral energy distribution). A (polynomial or other) fit to the data output by the simulation may be created for used in subsequent steps. The simulation need only be carried out once for each treatment system (e.g., LINAC machine, which may affect the x-ray energy spectrum created), as it is not dependent on the specific patient and target.

Next, in act 1204, dose distributions for a given patient and a given treatment target and surrounding tissue region (herein collectively the "target region") are calculated for the various beamlets (within a larger x-ray beam) intersecting with the target region from multiple angles and with different photon energies. This calculation is based on the preceding beamlet simulations, and takes a computational model of the target region, e.g., provided in the form of imaging data 1206 (e.g., CAT scans), as additional input. The imaging data 1206 may be annotated with a "contour mask" specifying the boundaries, or contours, of the treatment target (e.g., a tumor) as well as of any sensitive structures (e.g., lungs, spinal cord, etc.). The contour mask may be provided, for instance, by a physician drawing outlines on the images.

Once the dose distributions for the individual beamlets have been calculated, the treatment plane is initialized, that is, for each beamlet within the beam and for each angular position, spectral beam energies and associated intensities (or, equivalently, weightings of the spectral beam energies and an aggregate intensity) are determined. The initialization may be based on an ideal dose distribution 1210 provided as input. The ideal dose distribution may, for instance, specify a set uniform dose within the area of the treatment target, and zero dose in portions of the target region outside the treatment target. Initializing the treatment plan provides an initial guess for beamlet energies and intensities that achieve some approximation of the desired dose distribution, which may serve to "seed" the subsequent iterative optimization of the treatment plan. In some embodiments, this initial guess is computed with a least-squares algorithm to minimize the discrepancies (in the least-squares sense) between the ideal dose distribution and the actual dose distribution achieved with the guessed beamlet energies and intensities, aggregated across the treatment region.

Following initialization (in act 1208), the method 1200 proceeds into an optimization loop that involves randomly changing the beamlet intensities for the multiple energies (or, equivalently, changing the energy weightings and/or aggregate intensity for each beamlet) (act 1212), updating the dose distribution over the target region (aggregated over all beamlets from all directions) (act 1214), and evaluating (in act 1216) one or more dose criteria 1218 to determine whether the random changes constitute an improvement or worsening of the treatment plan. The dose criteria 1218 may, for instance, specify a total integral dose, a minimum dose to be applied to the target for effective treatment, a maximum dose tolerable for certain sensitive structures, a maximum tolerable skin dose, a maximum tolerable dose for normal (but not especially sensitive) tissues, minimum dose gradients from high tumor doses to nearby lower doses, and/or some metric of geometric conformity of the dose distribution to the target. These and other dose criteria, and methods of weighting and balancing them against each other, are familiar to those of ordinary skill in the art. The evaluated dose criteria may be fed back into the iterative optimization to determine whether to adopt or reverse the randomly made changes, and/or to guide the changes to beamlet intensities and energies made in the next iteration (e.g., by constraining the range from which such changes are randomly selected). Once the dose criteria 1218 are satisfied (or approximately satisfied within specified margins), or some other termination criterion (e.g., a time cut-off for the optimization process) is met, the final beamlet intensities may be converted to MLC control sequences that achieve those beamlet intensities. In alternative embodiments, the MLC control sequences are directly adjusted during the iterative process to optimize the corresponding beamlet intensities. The treatment plan can be output (in act 1220), e.g., by storing the final beamlet intensities (and/or corresponding MLC control sequences) and energies in a lookup table for subsequent use in treatment.

Energy-modulated radiation therapy adds a new dimension —namely, the spectral energy of the beam—to treatment design, beyond the consideration of beam orientation, field shape, and intensity. With spectral energy being added as an adjustable treatment parameter, the treatment planning method 1200 provides an approach to optimizing the tradeoffs between lower-energy verses higher-energy x-rays radiation to thereby optimize beam penetration and penumbra. With these enhanced capabilities, energy-modulated radiation therapy bears the potential to provide better treatment than is achievable using only one x-ray energy spectrum alone. For example, it may enable the treatment of targets smaller than a grain of rice as well as of microextensions extending out from tumors. Additionally, energy-modulated radiation therapy may facilitate treating tumors that abut extremely sensitive structures with x-rays (rather than the much costlier proton therapy). While conventional radiotherapy focuses on attacking the bulk of a tumor, energy-modulated radiotherapy may be used, in some embodiments, to target the microenvironment in and around the tumor, e.g., vasculature, lymphatics, and nerves, while sparing nearby tissues.

FIG. 13 is a schematic block diagram of an example computing system 1300 for performing treatment planning and/or treatment control in accordance with various embodiments (e.g., in accordance with method 1200 to generate a treatment plan and in accordance with method 900 to execute the treatment plan). The example computing system 1300 takes the form of a machine within which instructions for causing the machine to perform various of the methodologies discussed herein may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computing system 1300 includes a processor 1302 (e.g., a central processing unit (CPU), a graphics processing unit (GPU) or both), a main memory 1304 and a static memory 1306, which communicate with each other via a bus 1308. The computer system 1300 may further include a video display unit 1310 (e.g., a liquid crystal display (LCD) or a cathode ray tube (CRT)). The computer system 1300 also includes an alphanumeric input device 1312 (e.g., a keyboard), a cursor control device 1314 (e.g., a mouse), a disk drive unit 1316, a signal generation device 1118 (e.g., a speaker) and a network interface device 1320.

The disk drive unit 1316 includes a machine-readable medium 1322 on which are stored one or more sets of instructions and data structures (e.g., software) 1324 embodying or used by any one or more of the methodologies or functions described herein. The instructions 1324 may also reside, completely or at least partially, within the main memory 1304, static memory 1306, and/or within the processor 1302 during execution thereof by the computer system 1300, the main memory 1304 and the processor 1302 also constituting machine-readable media.

While the machine-readable medium 1322 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing or encoding data structures used by or associated with such instructions. The term "machine-readable medium" shall accordingly be taken to include, but not be limited to, solid-state memories, and optical and magnetic media. Specific examples of machine-readable media include non-volatile memory, including by way of example, semiconductor memory devices (e.g., Erasable Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks. All such machine-readable storage media are hardware devices suitable for storing data and/or instructions for a suitable period of time to enable use by the machine, and are therefore non-transitory.

The instructions 1324 may further be transmitted or received over a communications network 1326 using a transmission medium. The instructions 1324 may be transmitted using the network interface device 1320 and any one of a number of well-known transfer protocols (e.g., HTTP). Examples of communication networks include a LAN, a WAN, the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

Having described various aspects and features of the inventive subject matter, the following numbered examples are provided as illustrative embodiments:

1. A method for energy-modulated radiotherapy, the method comprising: generating at least one x-ray beam by directing an electron beam onto an x-ray converter target; and, while moving the at least one x-ray beam around a treatment target during irradiation of the treatment target, dynamically controlling a spectral energy distribution of the at least one x-ray beam as a function of at least angular position in accordance with a treatment plan by controlling an energy of the electron beam.

2. The method of example 1, wherein dynamically controlling the spectral energy distribution of the at least one x-ray beam comprises generating at least one energy distribution having a maximum energy of at least about 6 MeV and at least one energy distribution having a maximum energy of less than about 4 MeV.

3. The method of example 1 or example 2, wherein dynamically controlling the spectral energy distribution of the at least one x-ray beam comprises generating at least one energy distribution having a maximum energy of less than 2 MeV.

4. The method of any one of examples 1-3, wherein controlling the spectral energy distribution of the at least one x-ray beam comprises, for at least one of the angular positions, blending two spectral energy distributions having different maximum energies.

5. The method of any one of examples 1-4, wherein the electron beam is generated in a linear accelerator, and wherein dynamically controlling the energy of the electron beam comprises dynamically reducing the energy of the electron beam upon exiting the linear accelerator using a variable-thickness modulation layer placed in a path of the electron beam upstream of the x-ray converter target.

6. The method of any one of examples 1-4, wherein the electron beam is generated in a linear accelerator, and wherein dynamically controlling the energy of the electron beam comprises dynamically reducing the energy of the electron beam exiting the linear accelerator using a variable electric field.

7. The method of any one of examples 1-4, wherein the electron beam is generated in a linear accelerator, and wherein dynamically controlling the energy of the electron beam comprises dynamically reducing the energy of the electron beam exiting the linear accelerator by spreading the electron beam out by energy in a magnetic field and selectively absorbing higher-energy electrons from the beam.

8. The method of any one of examples 1-4, wherein the electron beam is generated in a multi-mode linear accelerator, and wherein dynamically controlling the energy of the electron beam comprises dynamically switching between the modes of the multi-mode accelerator.

9. The method of any one of examples 1-8, wherein the x-ray converter target is configured to rotate, an axis of rotation being displaced from the electron beam such that the position of incidence of the electron beam on the x-ray converter target periodically varies.

10. The method of any one of examples 1-9, wherein the x-ray converter target is in contact with a cooling liquid for heat dissipation.

11. The method of any one of examples 1-10, further comprising dynamically controlling at least one of an intensity, a beam width or shape, or a cross-sectional intensity distribution of the at least one x-ray beam as a function of at least angular position.

12. The method of example 11, wherein the intensity, beam width or shape, or cross-sectional intensity distribution is controlled using a multi-leaf collimator, the method further comprising using the multi-leaf collimator to monitor an intensity or energy of the x-ray beam.

13. The method of any one of examples 1-12, further comprising using one or more computer processors to create the treatment plan, the treatment plan specifying a spectral energy distribution of the at least one x-ray beam as a function of at least the angular position that optimizes a radiation dose for at least one of target conformity, high dose gradients between target and non-target regions, low dose to critical structures, low dose to skin, low dose to normal tissue, or low total integral dose.

14. An energy-modulating x-ray converter target module for use in a linear accelerator device, the module comprising: a variable-thickness energy-modulation layer operatively to be placed in a path of an electron beam generated by the linear accelerator device to reduce an energy of the electron beam; an x-ray converter target layer operatively to be placed in the path of the electron beam downstream of the energy-modulation layer to generate high-energy x-rays from the incident electron beam; and a mechanism operatively to move at least one of the energy-modulation layer or the x-ray converter target layer to alter a thickness of the energy-modulation layer encountered by the electron beam.

15. The energy-modulating x-ray converter target module of example 14, further comprising: a housing enclosing the x-ray converter target layer, wherein the housing is operatively filled with water forming a first layer preceding the x-ray converter target layer and a second layer following the x-ray converter target layer.

16. The energy-modulating x-ray converter target module of example 15, wherein the first layer forms the energy-modulation layer, and wherein the mechanism is to move the x-ray converter target layer in a direction of the incident electron beam to thereby alter the thickness of the energy-modulation layer.

17. The energy-modulating x-ray converter target module of example 15 or example 16, wherein the water is flown past the x-ray converter target layer to cool the x-ray converter target layer.

18. The energy-modulating x-ray converter target module of example 14, wherein the energy-modulation layer increases in thickness along a direction perpendicular to a direction of incidence of the electron beam, and wherein the mechanism is to move the energy-modulation layer parallel to the direction perpendicular to the direction of incidence to thereby alter the thickness of the energy-modulation layer encountered by the electron beam.

19. The energy-modulating x-ray converter target module of example 18, wherein the x-ray converter target layer decreases in thickness in the direction in which the energy-modulation layer increases in thickness.

20. A computer-readable storage device storing instructions for execution by one or more computer processors, the instructions, when executed, causing the one or more computer processors to perform operations for planning x-ray treatment of a target within a patient, the operations comprising: calculating, based at least in part on a data model of the target and surrounding tissues, dose distributions for a plurality of beamlets, the plurality of beamlets comprising beamlets incident onto the target from a plurality of directions and, for each direction, at least two beamlets having at least two different respective spectral energy distributions; and optimizing intensities of the plurality of beamlets, based on the calculated dose distributions, for one or more dose criteria.

21. The computer-readable storage device of example 20, wherein optimizing the intensities of the plurality of beamlets comprises initializing the intensities, and iteratively testing an impact of random changes to the intensity of each beamlet on an aggregate dose distribution as compared against the dose criteria.

22. The computer-readable storage device of example 20, wherein optimizing the intensities of the plurality of beamlets comprises initializing the intensities, and iteratively testing an impact of random changes, for each direction, to relative weightings between the at least two beamlets having the at least two different respective spectral energy distributions on an aggregate dose distribution as compared against the dose criteria.

23. The computer-readable storage device of any of examples 20-22, wherein the at least two different spectral energy distributions have respective maximum energies of at least about 6 MeV and of less than about 4 MeV.

24. An energy-modulated radiotherapy system comprising: a linear accelerator operatively generating an electron beam to be directed onto an x-ray converter target to generate an x-ray beam; energy-modulation means for dynamically modifying an energy of the electron beam to thereby dynamically control a spectral energy distribution of the x-ray beam; a gantry operatively moving the x-ray beam around a treatment target; and a control system operatively to control the energy-modulation means to dynamically control the spectral energy distribution of the x-ray beam as a function of at least angular position in accordance with a treatment plan.

25. The system of example 24, further comprising a multi-leaf collimator placed in the x-ray beam, the multi-leaf collimator configurable to adjust an intensity, beam width or shape, or cross-sectional intensity distribution of the x-ray beam, the control system further configured to operatively control the multi-leaf collimator in accordance with the treatment plan.

26. The system of example 24 or example 25, wherein the energy-modulation means comprises at least one of a variable-thickness modulation layer placed in a path of the electron beam upstream of the x-ray converter target, a variable electric field reducing the energy of the electron beam exiting the linear accelerator, an electron-absorber selectively absorbing higher-energy electrons from the electron beam, or a switch for switching between multiple modes of the linear accelerator.

Although embodiments have been described with reference to specific example embodiments, it will be evident that various modifications and changes may be made to these embodiments without departing from the broader scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This description, therefore, is not to be taken in a limiting sense, and the scope of various embodiments is defined only by the appended claims, along with the full range of equivalents to which such claims are entitled.

What is claimed is:

1. A method for energy-modulated radiotherapy, the method comprising:
generating at least one x-ray beam by directing an electron beam onto an x-ray converter target;
while moving the at least one x-ray beam around a treatment target during irradiation of the treatment target,
dynamically controlling a spectral energy distribution of the at least one x-ray beam as a function of at least angular position in accordance with a treatment plan by dynamically controlling an energy of the electron beam;
dynamically controlling at least one of an intensity, beam width or shape, or cross-sectional intensity distribution of the at least one x-ray beam as a function of at least the angular position using a multi-leaf collimator; and
monitoring the intensity or energy of the at least one x-ray beam using the multi-leaf collimator.

2. The method of claim 1, wherein dynamically controlling the spectral energy distribution of the at least one x-ray beam comprises generating a first energy distribution having a maximum energy of at least 6 MeV and a second energy distribution having a maximum energy of less than 4 MeV.

3. The method of claim 1, wherein dynamically controlling the spectral energy distribution of the at least one x-ray beam comprises generating at least one energy distribution having a maximum energy of less than 2 MeV.

4. The method of claim 1, wherein controlling the spectral energy distribution of the at least one x-ray beam comprises, for at least one angular position, blending two spectral energy distributions having different maximum energies.

5. The method of claim 1, wherein the electron beam is generated in a linear accelerator, and wherein dynamically controlling the energy of the electron beam comprises dynamically reducing the energy of the electron beam upon exiting the linear accelerator using a variable-thickness modulation layer placed in a path of the electron beam upstream of the x-ray converter target.

6. The method of claim 1, wherein the electron beam is generated in a linear accelerator, and wherein dynamically controlling the energy of the electron beam comprises dynamically reducing the energy of the electron beam exiting the linear accelerator using a variable electric field.

7. The method of claim 1, wherein the electron beam is generated in a linear accelerator, and wherein dynamically controlling the energy of the electron beam comprises dynamically reducing the energy of the electron beam exiting the linear accelerator by spreading the electron beam out by energy in a magnetic field and selectively absorbing higher-energy electrons from the beam.

8. The method of claim 1, wherein the electron beam is generated in a multi-mode linear accelerator, and wherein dynamically controlling the energy of the electron beam comprises dynamically switching between modes of the multi-mode accelerator.

9. The method of claim 1, wherein the x-ray converter target is configured to rotate, an axis of rotation being displaced from the electron beam such that the position of incidence of the electron beam on the x-ray converter target periodically varies.

10. The method of claim 1, wherein the x-ray converter target is in contact with a cooling liquid for heat dissipation.

11. The method of claim 1, further comprising using one or more computer processors to create the treatment plan, the treatment plan specifying the spectral energy distribution of the at least one x-ray beam as a function of at least the angular position to optimize a radiation dose for at least one of target conformity, high dose gradients between target and non-target regions, low dose to critical structures, low dose to skin, low dose to normal tissue, or low total integral dose.

12. An energy-modulating x-ray converter target module for use in a linear accelerator device, the module comprising:
an x-ray converter target layer operatively to be placed in a path of an electron beam to generate high-energy x-rays from the electron beam;
a housing enclosing the x-ray converter target layer, wherein the housing is operatively filled with liquid forming a first layer preceding the x-ray converter target layer and a second layer following the x-ray converter target layer, the first layer serving as a variable-thickness energy-modulation layer; and
a mechanism operatively to move the x-ray converter target layer within the housing in a direction of the electron beam to alter a thickness of the energy-modulation layer encountered by the electron beam.

13. The energy-modulating x-ray converter target module of claim 12,
wherein the liquid is water.

14. The energy-modulating x-ray converter target module of claim 12, wherein the liquid is flowed past the x-ray converter target layer to cool the x-ray converter target layer.

15. A computer-readable storage device storing instructions for execution by one or more computer processors, the instructions, when executed, causing the one or more computer processors to perform operations for planning x-ray treatment of a target within a patient, the operations comprising:

calculating, based at least in part on a data model of the target and surrounding tissues, dose distributions for a plurality of beamlets, the plurality of beamlets comprising beamlets incident onto the target from a plurality of directions and, for each direction, at least two beamlets having at least two different respective spectral energy distributions; and optimizing intensities of the plurality of beamlets, based on the calculated dose distributions, for one or more dose criteria, wherein optimizing the intensities of the plurality of beamlets comprises initializing the intensities, and iteratively testing an impact of random changes, for each direction, to relative weightings between the at least two beamlets having the at least two different respective spectral energy distributions on an aggregate dose distribution as compared against the dose criteria.

16. The computer-readable storage device of claim 15, wherein optimizing the intensities of the plurality of beamlets comprises initializing the intensities, and iteratively testing an impact of random changes to the intensity of each beamlet on an aggregate dose distribution as compared against the dose criteria.

17. The computer-readable storage device of claim 15, wherein the at least two different spectral energy distributions have respective maximum energies of at least 6 MeV and of less than 4 MeV.

* * * * *